Oct. 27, 1959 I. MACKAY Plant Pat. 1,874
CHRYSANTHEMUM PLANT
Filed Feb. 2, 1959
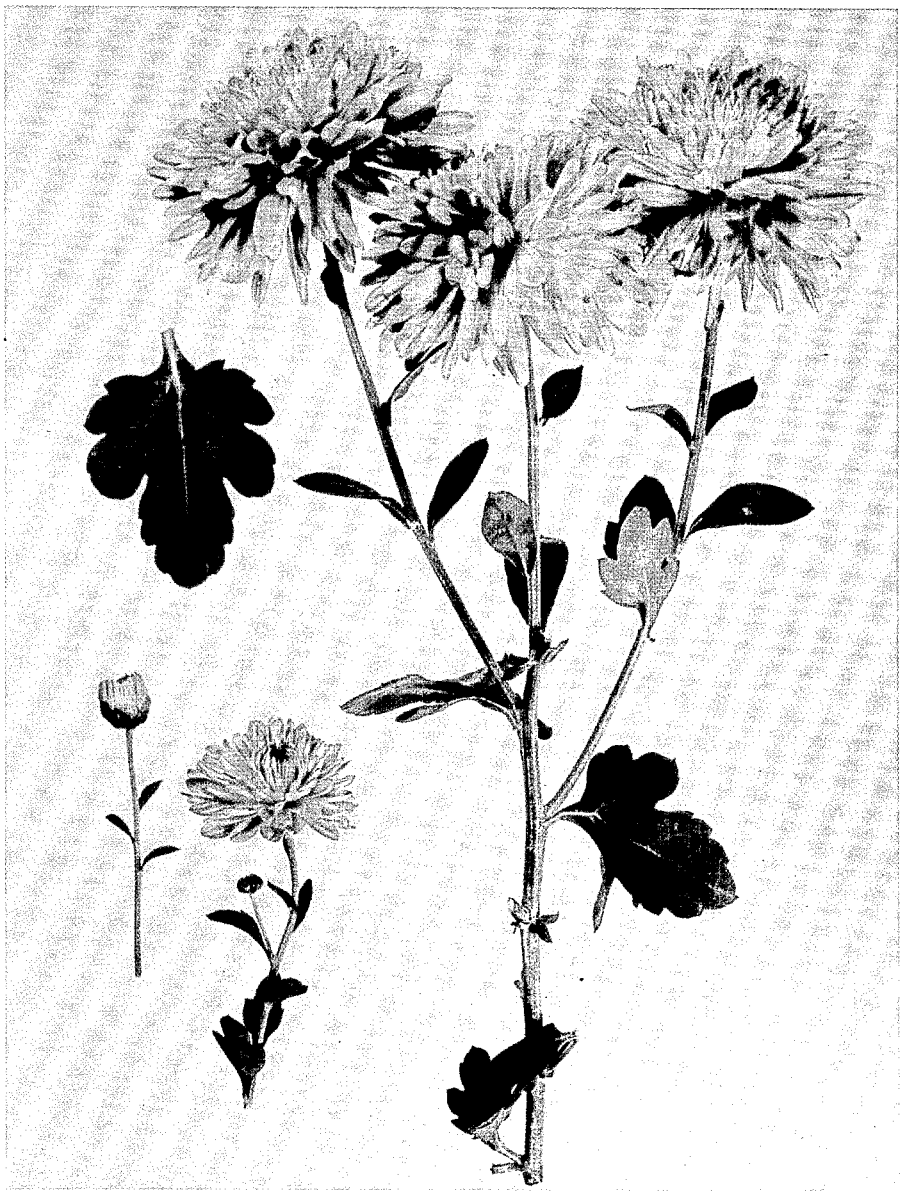
INVENTOR
Ian Mackay
BY Robb & Robb
ATTORNEYS United States Patent Office Plant Pat. 1,874
Patented Oct. 27, 1959

1,874

CHRYSANTHEMUM PLANT

Ian Mackay, Kirkwood, Pa., assignor to The Conrad-Pyle Company, West Grove, Pa., a corporation of Pennsylvania Application February 2, 1959, Serial No. 790,402
1 Claim. (Cl. 47—60)

The present invention relates to a new and distinct variety of chrysanthemum plant of the decorative cushion type, which was originated by me by crossing the variety "Edith" (unpatented) with the variety "Midnight Cushion" (unpatented).

The primary objective of this breeding was to produce a new chrysanthemum variety combining the interesting color tones of the parent variety "Edith" with the plant habit and darker color tones of the parent variety "Midnight Cushion." This objective was fully achieved, along with other improvements, as evidenced by the following unique combination of characteristics which are outstanding in the new variety and which differentiate it from its parents, as well as from all other varieties of which I am aware:

(1) A compact, well-branched, vigorous habit of growth;
(2) Clean, dark green foliage;
(3) Very double blooms of good form; and
(4) A distinctive Lilac Purple general color tonality of the blooms.

Asexual reproduction of the new variety by cuttings, as performed at West Grove, Pennsylvania, shows that the aforementioned characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character.

The following is a detailed description of my new variety, with color terminology in accordance with the Horticultural Colour Chart of the Royal Horticultural Society, except where general color terms of ordinary dictionary significance are obvious, as based upon observations made at West Grove, Pennsylvania:

Parentage: Seedling.
*Seed parent.*—"Edith."
*Pollen parent.*—"Midnight Cushion."
Type: Cushion; hardy, medium height; outdoor; seedling; for garden decoration.
Classification:
*Horticultural.*—Decorative.
*Botanical.*—Hortorum.
Propagation: Holds its distinguishing characteristics through succeeding propagations by cuttings.

*Flower*

Flowers borne: Several to stem; in pyramidal clusters; on stems of medium length and normal strength.
Quantity of bloom: Abundant, outdoors.
Continuity: Continuous during September and October.
Fragrance: Strong. Nature—chrysanthemum.

This description was made from a first year plant and bloom grown outdoors in the month of October at West Grove, Pennsylvania:

Bud:
*Peduncle.*—Medium length; erect; rough; numerous hairs. Color—Willow Green, Plate 000862.
*Before calyx breaks.*—Size—medium. Form—oval.
*As calyx breaks.*—Color—Magnolia Purple, Plate 030/1.

*As petals open.*—Color: inside—Magnolia Purple, Plate 030; outside—Magnolia Purple, Plate 030/2.
*Opening.*—Opens up well in all weather.
Bloom:
*Size (when fully open).*—Medium large; 3½ inches in diameter.
*Form.*—Globular; with full center.
*Petalage.*—Fully double. Outer petals—straight; convex in transverse section. Inner petals—straight; concave in cross section.
*Color.*—Outer petals: inner surface—Lilac Purple, Plate 031/1; outer surface—Cobalt Violet, Plate 634/3, overlaid along the midrib with Petunia Purple, Plate 32/2. Intermediate petals: inner surface—Lilac Purple, Plate 031; outer surface—Cobalt Violet, Plate 634/3, overlaid along the midrib with Petunia Purple, Plate 32/2. Inner petals: inner surface—Pastel Mauve, Plate 433/3 at base, fading to Lilac Purple, Plate 031/1 at apex; outer surface—Pastel Mauve, Plate 433/3 at base, shading to Orchid Purple, Plate 31/3 at tip.
*Color change with age.*—None.
Ray flower petals: Medium stiff.
*Inside.*—Velvety.
*Outside.*—Shiny.
*Size.*—Outer—medium long. Intermediate—medium. Inner—short.
*Shape.*—Elliptic.
Disc flower petals: Few; medium size; medium length; medium thick. Color—Canary Yellow, Plate 2.
Flower longevity:
*On bush in garden.*—Long duration.
*Cut flowers grown outdoors and kept at living-room temperature.*—Medium duration.

*Genital organs*

Anthers: Few.
Stigma: Color—yellow-white.

*Plant*

Growth habit (as compared with other varieties grown simultaneously under the same cultural conditions in the field): Bushy; much-branched; compact; medium height in first year of growth; medium broad in first year of growth; height usually the same as spread.
Vigor: From free to vigorous.
Stems: Color—Willow Green, Plate 000862.
Foliage:
*Size.*—Medium.
*Quantity.*—Normal.
*Texture.*—Medium leathery.
*Upper surface.*—Rough; dull.
*Under surface.*—Hirsute.
*Shape.*—Ovate, with apex acute.
*Base.*—Obtuse.
*Margin.*—Parted.
*Veins.*—Upper surface — medium prominence. Lower surface—prominent.
*Color.*—Upper side—Spinach Green, Plate 0960. Lower side—Lavender Green, Plate 000761.

I claim:

A new and distinctive variety of chrysanthemum plant of the decorative cushion type, substantially as herein shown and described, characterized particularly as to novelty by the unique combination of a compact, well-branched, vigorous habit of growth, clean, dark green foliage, very double blooms of good form, and a distinctive Lilac Purple general color tonality of the flowers.

No references cited.

UNITED STATES PATENT OFFICE

CERTIFICATE OF CORRECTION

Plant
Patent No. 1,874 October 27, 1959

Ian Mackay

It is hereby certified that error appears in the above numbered patent requiring correction and that the said Letters Patent should read as corrected below.

In the grant, lines 2 and 13, and in the heading to the printed specification, lines 3 and 4, name of assignee, for "The Conrad-Pyle Company", each occurrence, read -- The Conard-Pyle Company --.

Signed and sealed this 5th day of January 1960.

(SEAL)
Attest:

KARL H. AXLINE
Attesting Officer

ROBERT C. WATSON
Commissioner of Patents